(12) United States Patent
Bolk et al.

(10) Patent No.: US 6,642,001 B1
(45) Date of Patent: Nov. 4, 2003

(54) GENERIC SBE-FRET PROTOCOL

(75) Inventors: Stacey Bolk, West Roxbury, MA (US); Joel N. Hirschhorn, Newton, MA (US); James S. Ireland, Somerville, MA (US); Eric S. Lander, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/615,216

(22) Filed: Jul. 13, 2000

Related U.S. Application Data

(60) Provisional application No. 60/143,598, filed on Jul. 13, 1999, and provisional application No. 60/161,975, filed on Oct. 28, 1999.

(51) Int. Cl.[7] .................. C12Q 1/68; C12P 19/34; G01N 33/566; C07H 21/00
(52) U.S. Cl. .................. 435/6; 435/91.2; 935/77; 935/78; 536/25.32; 436/501
(58) Field of Search .................. 435/6, 91.2; 436/501; 935/77, 78; 536/25.32

(56) References Cited

U.S. PATENT DOCUMENTS

| | | | |
|---|---|---|---|
| 4,868,103 A | 9/1989 | Stavrianopoulos et al. | 435/5 |
| 4,996,143 A | 2/1991 | Heller et al. | 435/6 |
| 5,650,277 A | 7/1997 | Navot et al. | 435/6 |
| 5,710,028 A | 1/1998 | Eyal et al. | 435/91.1 |
| 5,888,778 A * | 3/1999 | Shuber | 435/91.1 |
| 5,888,819 A | 3/1999 | Goelet et al. | 435/5 |
| 5,945,283 A | 8/1999 | Kwok et al. | 435/6 |
| 5,981,176 A | 11/1999 | Wallace | 435/6 |
| 6,270,967 B1 * | 8/2001 | Whitcombe et al. | 435/6 |

FOREIGN PATENT DOCUMENTS

| | | | | |
|---|---|---|---|---|
| EP | 0 124 221 | 11/1984 | | C12Q/1/68 |
| EP | 0 229 943 | 7/1987 | | C12Q/1/68 |
| GB | 2 312 747 | 11/1997 | | C12Q/1/68 |
| WO | WO 92/14845 | 9/1992 | | C12Q/1/68 |
| WO | WO 92/15712 | 9/1992 | | C12Q/1/68 |
| WO | WO 93/25563 | 12/1993 | | C07H/15/12 |
| WO | WO 97/22719 | 6/1997 | | |
| WO | WO 97/31256 | 8/1997 | | |
| WO | WO 99/10538 | 3/1999 | | C12Q/1/68 |
| WO | WO 99/27137 | 6/1999 | | C12Q/1/68 |

OTHER PUBLICATIONS

Chen, Xiangning et al., "Fluorescence energy transfer detection as a homogeneous DNA diagnostic method," *Proc. Natl. Acad. Sci. USA*, 94:10756–10761 (1997).

Yaron A., et al., "Intramolecularly Quenched Fluorogenic Substrates for Hydrolytic Enzymes," *Analytical Biochemistry*, 95:228–235 (1979).

Bolk, S. et al., "High–throughput SNP genotyping using single–base extension," *American Journal of Human Genetics*, 65(4):A97 (Abstract 509) (1999).

Pastinen, Tomi et al., "Minisequencing: A Specific Tool for DNA Analysis and Diagnostics on Oligonucleotide Arrays," *Genome Research*, 7(6):606–614 (1997).

Chen, Xiangning et al., "Homogeneous genotyping assays for single nucleotide polymorphisms with fluorescence resonance energy transfer detection," *Genetic Analysis: Biomolecular Engineering*, 14:157–163 (1999).

* cited by examiner

*Primary Examiner*—Jeffrey Siew
*Assistant Examiner*—Joyce Tung
(74) *Attorney, Agent, or Firm*—Hamilton, Brook, Smith & Reynolds, P.C.

(57) ABSTRACT

The present invention is drawn to methods for detection, quantitation and analysis of nucleotides of interest in nucleic acid sequences of interest using single base extension and fluorescence resonance energy transfer and generic donor molecule-labeled detection probes.

45 Claims, 5 Drawing Sheets

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Detection probe

<400> SEQUENCE: 1
gggccgggac cgaccgcgcg                                           20

<210> SEQ ID NO 2
<211> LENGTH: 20
<212> TYPE: DNA
<213> ORGANISM: Artificial Sequence
<220> FEATURE:
<223> OTHER INFORMATION: Constant region

<400> SEQUENCE: 2

```
cgcgcggtcg gtcccggccc                                          20

<210> SEQ ID NO 3
<211> LENGTH: 21
<212> TYPE: DNA
<213> ORGANISM: Artificial Sequence
<220> FEATURE:
<223> OTHER INFORMATION: Locus F13Alu4

<400> SEQUENCE: 3
tgtgacagtt sagtttacca a                                        21

<210> SEQ ID NO 4
<211> LENGTH: 21
<212> TYPE: DNA
<213> ORGANISM: Artificial Sequence
<220> FEATURE:
<223> OTHER INFORMATION: Locus PAI2u4

<400> SEQUENCE: 4
agataaccaa stgcatttta t                                        21

<210> SEQ ID NO 5
<211> LENGTH: 21
<212> TYPE: DNA
<213> ORGANISM: Artificial Sequence
<220> FEATURE:
<223> OTHER INFORMATION: Locus F5u18

<400> SEQUENCE: 5
aaataaggca sataagccct t                                        21

<210> SEQ ID NO 6
<211> LENGTH: 21
<212> TYPE: DNA
<213> ORGANISM: Artificial Sequence
<220> FEATURE:
<223> OTHER INFORMATION: Locus F5u36

<400> SEQUENCE: 6
caacatgcct rtggacatga g                                        21
```

US 6,642,001 B1

GENERIC SBE-FRET PROTOCOL

RELATED APPLICATIONS

This application claims the benefit of U.S. Provisional Application No.: 60/143,598, filed Jul. 13, 1999 and U.S. Provisional Application No.: 60/161,1461,975, filed Oct. 28, 1999, the entire teachings of which are incorporated herein by reference.

BACKGROUND OF THE INVENTION

Nucleic acid analysis techniques that identify alterations or polymorphisms within known sequences are useful in many aspects of scientific, medical and forensic fields. For example, these techniques can be used in the genotyping of individuals in order to diagnose hereditary diseases or provide prognosis based on known genetic lesions. These techniques can also be used for clinical purposes such as tissue typing for histocompatibility or for forensic purposes such as identity or paternity determination. Furthermore, nucleic acid analysis techniques can be used for the identification of organisms or to distinguish or identify pathogenic organisms or infectious agents. In addition, these techniques are useful in the identification and monitoring of genetically modified agricultural organisms such as crops and livestock. As genomic sequence of organisms from bacteria to humans become known, the need for nucleic acid analysis techniques that are rapid and inexpensive increases.

Nucleic acids are readily analyzed and quantitated using probe-based assays. The presence of nucleic acid sequences from bacteria, fungi, viruses or other organisms is assayed with nucleic acid probes and such probes are also useful in examining genotypes, genetically-based disease states or other clinical conditions of interest. Genotypes of interest include, for example, point mutations, deletions, insertions and inversions. Furthermore, these assays are useful to detect and monitor polymorphisms within nucleic acid sequences of interest.

Probe-based assays typically rely on nucleic acid hybridization. Sequence differences of a single base (e.g., point mutation) in very short oligomers (e.g., <10 base pairs ("bp") can be sufficient to enable the discrimination of the hybridization to complementary nucleic acid target sequences as compared with non-target sequences. However, nucleic acid probes of greater than 10 bp in length are often preferred or required to obtain the sequence specificity necessary to correctly identify a unique organism, disease state or clinical condition of interest.

Using hybridization assays, large numbers of patient samples can be screened for a large number of loci of interest. Yet, given the requirement that each of the many different probes in the assay exhibit a very high degree of specificity for a specific target nucleic acid sequence under the same or similar conditions of stringency it is often difficult to assay more than one sample and or more than one locus of interest (e.g., multiplex assays).

An alternative method for identifying and analyzing one or more polymorphisms is based on single-base extension (SBE) of a fluorescently-labeled primer coupled with fluorescence resonance energy transfer (FRET) between the label of the added base and the label of the primer. Typically, the method, such as that described by Chen et al., (*PNAS* 94:10756–61 (1997), incorporated herein by reference) uses a locus-specific oligonucleotide primer labeled on the 5' terminus with 5-carboxyfluorescein (FAM). This labeled primer is designed so that the 3' end is immediately adjacent to the polymorphic site of interest. The labeled primer is hybridized to the locus, and single base extension of the labeled primer is performed with fluorescently labeled dideoxyribonucleotides (ddNTPs) in dye-terminator sequencing fashion, except that no deoxyribonucleotides are present. An increase in fluorescence of the added ddNTP in response to excitation at the wavelength of the labeled primer is used to infer the identity of the added nucleotide. However, this method requires the use of labeled target-specific oligonucleotide primers for each polymorphism assayed.

SUMMARY OF THE INVENTION

The present invention relates to a method for determining and analyzing polymorphisms which eliminates the need for labeled target-specific primers. In one embodiment of the present invention, traditional SBE/FRET protocols are modified in that unlabeled primers are used which comprise a generic or constant sequence on the 5' end of the primer. The generic sequence is complementary to a fluorescently-labeled detection probe (e.g., a FAM-labeled detection probe). Thus, identical FAM-labeled detection probes can be used for any primer with the generic sequence on the 5' end. This obviates the need for specialized labeled primers and allows for a generic SBE/FRET assay. FRET occurs if the detection probe is hybridized to a primer having a nucleotide with a fluorescent acceptor molecule attached thereto (a labeled nucleotide), wherein said labeled nucleotide was added to the primer by template-dependent synthesis, such that it is complementary to the nucleotide of interest or polymorphic nucleotide of interest. The present invention retains all of the advantages and uses of standard SBE/FRET, and has the additional advantage of not requiring expensive, target specific primers that are labeled with donor fluorescent molecules. Furthermore, the present invention has the advantage that the detection probe can be reused.

In one embodiment, the present invention is drawn to a method of determining the identity of a nucleotide at a specific location within a nucleic acid sequence of interest. The present invention is also drawn to a method for determining the identity of a nucleotide of interest at one or more polymorphic sites in at least one nucleic acid sequence of interest. The method comprises forming at least one detection complex comprising a generic detection probe comprising a detection sequence and a donor fluorescent molecule, and an extended primer wherein the primer is extended with a labeled nucleotide by template-dependent synthesis, using the nucleic acid molecule of interest, and more particularly the nucleotide of interest, as the template. The primer of the present invention comprises a variable nucleic acid sequence and a nucleic acid sequence (a generic or constant sequence) which hybridizes to (e.g., is complimentary to) said detection sequence. In the method of the present invention, the variable portion of said primer hybridizes to a region of the nucleic acid sequence of interest immediately adjacent to a nucleotide of interest and said labeled nucleotide is complementary to said nucleotide of interest. In the method of the present invention, the detection complexes formed are detected by fluorescence resonance energy transfer from the donor fluorescent molecule to the acceptor fluorescent molecule. In one embodiment, the nucleic acid sequence of interest is also part of the detection complex.

Thus, in the method of the present invention, one or more nucleotides of interest (e.g., at a polymorphic site) in at least one nucleic acid sequence of interest is detected by fluorescence resonance energy transfer from a donor fluorescent molecule on a generic detection probe to an acceptor fluorescent molecule on an extended target-specific primer. For example, when different acceptor fluorescent molecules are used to label the different nucleotides used in the single base extension reaction, the resulting fluorescence resonance energy transfer when a given labeled nucleotide is present in the detection complex with the donor fluorescent molecule, allows differentiation between polymorphic nucleotides at the extended position.

The present invention is further drawn to a detection probe comprising a detection sequence of about 10 to about 40 nucleotides in length, wherein said probe is labeled with a donor fluorescent molecule. In one embodiment the present invention is drawn to a detection probe comprising FAM-GGGCCGGGACCGACCGCGCG (SEQ ID NO: 1).

The present invention is also drawn to a primer comprising a nucleic acid sequence of about 10 to about 110 nucleotides in length, wherein said primer comprises a variable region and a constant region. For example, in one embodiment of the present invention, the constant region comprises CGCGCGGTCGGTCCCGGCCC (SEQ ID NO:2).

The present invention is further drawn to a kit for the detection of at least one nucleotide of interest (e.g., at a polymorphic site) in at least one nucleic acid sequence of interest. The kit of the present invention comprises at least one detection probe, wherein each detection probe comprises a detection sequence and a donor fluorescent molecule. The kit of the present invention can further comprise one or more primers, wherein each primer comprises a variable region and a constant region, such that said variable region hybridizes under appropriate conditions immediately adjacent to a nucleotide of interest in a nucleic acid sequence of interest, and wherein said constant region of said primer hybridizes to a given detection probe (preferably to the detection sequence). The kit of the present invention can further comprise dideoxynucleotides labeled with a fluorescent acceptor molecule.

This invention relates to methods, kits and compositions suitable for the improved detection, quantitation and analysis. of nucleic acid target sequences and polymorphisms using single base extension, preferably in conjunction with fluorescence resonance energy transfer. The invention is more specifically directed to methods, kits and compositions suitable for specifically detecting, quantitating or identifying one or more target nucleic acids in a sample, or at least one nucleotide of interest (e.g., at a specific site or wherein the nucleotide of interest is a polymorphic nucleotide) within a nucleic acid sequence, even in the presence of non-target sequences. The present invention allows the use of generic detection probes in the detection, quantitation and analysis of multiple nucleic acid target sequences, polymorphisms and nucleotides of interest. The present invention further allows for the reuse of said detection probes. The present invention is particularly well suited for sensitive and reliable SBE/FRET-based assays designed to analyze point mutations. The methods, kits and compositions of this invention also find utility for the detection, quantitation or analysis of organisms (micro-organisms), viruses, fungi and genetically-based clinical or forensic conditions of interest.

DETAILED DESCRIPTION OF THE INVENTION

Figure 1:
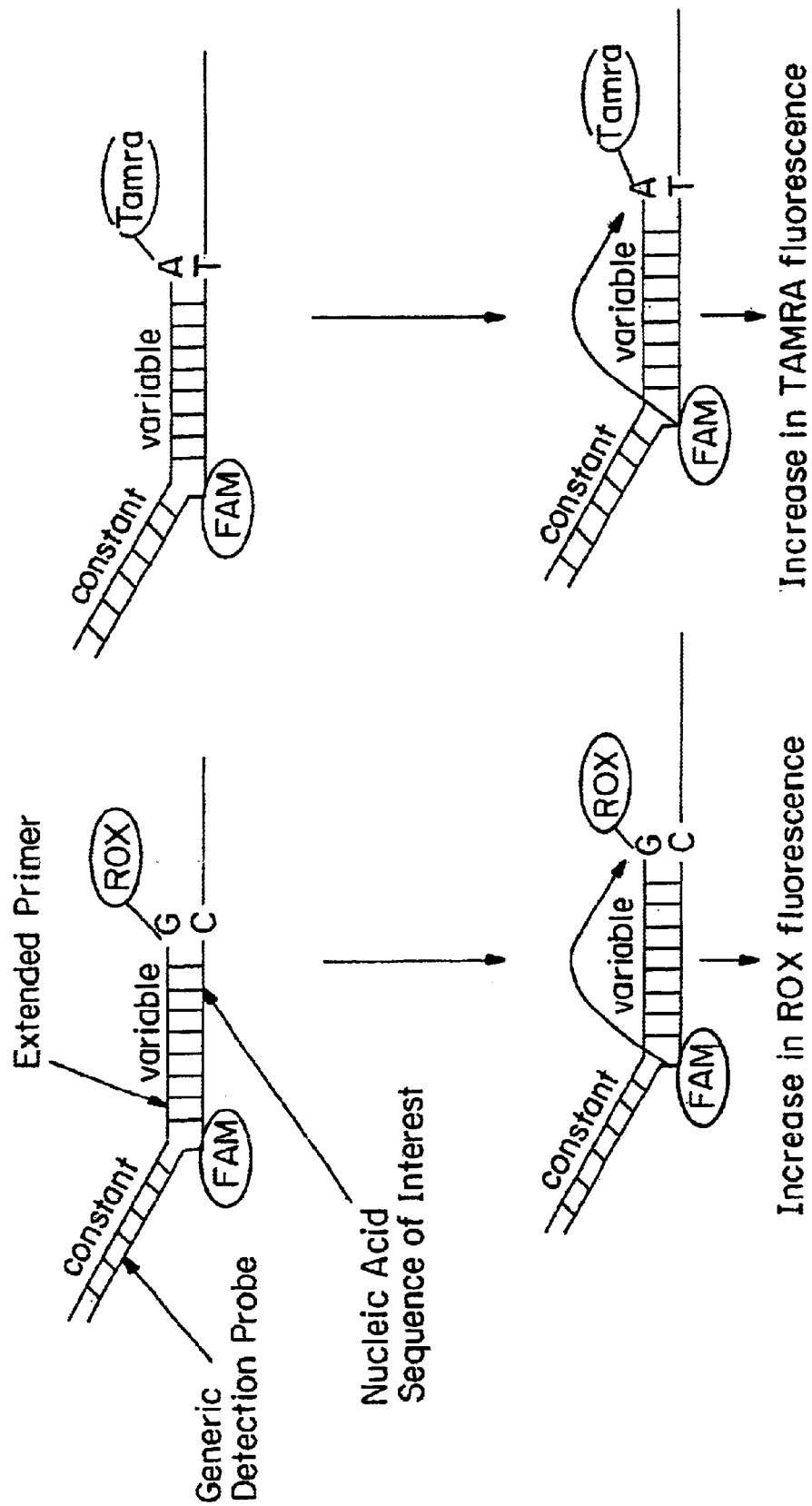
FIG. 1 is a schematic representation of the method of the present invention.

This invention relates to methods suitable for the detection, quantitation and analysis of nucleic acid target sequences using fluorescence resonance energy transfer. The invention is more specifically directed to methods of forming target-specific detection complexes comprising an extended primer and a detection probe. The primer comprises a variable region and a constant region, such that the variable region hybridizes to a target nucleic acid sequence immediately adjacent to a polymorphic nucleotide or nucleotide of interest. The primer hybridizes to the target nucleic acid sequence under conditions suitable for the variable acid portion of the primer to direct template-dependent addition of a single nucleotide labeled with a fluorescent acceptor molecule, thus generating an extended primer. The constant region of said primer hybridizes to said detection probe. In the method of the present invention, the detection probe is labeled with a donor fluorescent molecule and comprises a detection sequence to which the constant region of the primer hybridizes. The detection complex is detected, e.g. by FRET, wherein the sample is interrogated with an appropriate wavelength of light, such that the donor fluorescent molecule is excited, and emitted light is measured at a wavelength suitable to detect emission from the acceptor fluorescent molecule. In one embodiment of the invention, the detection complex comprises an extended primer hybridized to a detection probe. In another embodiment the primer is also hybridized to the target nucleic acid sequence (see FIG. 1). It is understood that in the alternative, the detection probe can comprise an acceptor fluorescent molecule. In these alternative embodiments, the single added nucleotide comprises a donor fluorescent molecule.

The invention is further directed to detection probes and primers for use in said methods and kits containing said detection probes and primers suitable to form said complexes in the presence of a target nucleic acid sequence. In one embodiment, the detection probes and constant region of said primers comprise guanine/cysteine rich sequence. In another embodiment of the present invention, the detection probe and the constant region of said primer comprises SEQ ID NO: 1 and SEQ ID NO: 2, respectively.

As used herein, the term "detection probe" is defined as any oligomer, comprising nucleic acid subunits, wherein said oligomer is suitable for hybridizing to the constant region of a primer of the present invention. Detection probes include oligomers of peptide nucleic acid, ribonucleic acid, deoxyribonucleic acid, chimeric oligomers or linked polymers. Chimeric oligomers comprise nucleic acid subunits of more than one type (e.g., DNA with RNA subunits, DNA with PNA subunits, RNA with PNA subunits or all three subunits). Linked polymers comprise oligomers of one type of subunit linked to an oligomer of the same or different subunit. Methods of linking oligomers comprising DNA, RNA or PNA are well known in the art. The preferred length of the detection probe is about 6 to about 50 nucleotides (nucleic acids) in length. More preferably, the detection probe is about 10 to about 25 nucleotides in length. Most preferably, the detection probe is about 20 nucleotides in length.

As used herein, "primer" is defined as an oligomer comprising a variable region and a constant region. The composition of the primer may be nucleic acid (e.g., ribonucleic acid or deoxyribonucleic acid) or a combination of peptide nucleic acid (PNA) and nucleic acid. For example, the target specific region of the primer can be RNA or DNA and the constant region can be nucleic acid or PNA.

As used herein, the term "Peptide Nucleic Acid" or "PNA" includes compounds referred to as Peptide Nucleic Acids in U.S. Pat. Nos. 5,539,082, 5,527,675, 5,623,049 or 5,714,331 (the entire teachings of which are incorporated herein by reference). Further modifications of PNA are well known in the art.

The variable region of the primer is the sequence-specific recognition portion of the primer. Therefore, the variable region is a sequence of nucleotides designed to hybridize to a target nucleic acid sequence, if present, under suitable hybridization conditions. The length of the variable region will generally be chosen such that a complex is formed between the variable region and the target sequence, wherein the complex is suitable to allow the primer to direct template-dependent synthesis. The variable region suitable for the practice of this invention will generally have a length of about 5 and about 60 nucleotides. Preferably, the variable region will be about 10 to about 40 nucleotides. Most preferably, the variable region will be about 15 nucleotides. The variable region of the primer will generally have a nucleotide sequence which is complementary to a region of nucleic acid sequence immediately adjacent to the polymorphic nucleotide or nucleotide of interest. The constant region of the primer is that portion which hybridizes to the detection probe. The constant region of the primer and the detection sequence of the detection probe may be of different lengths, but are preferably the same length.

In one embodiment of the present invention, the sequence and length of the detection probe and the complementary constant region are chosen to yield a melting temperature (Tm) greater than that of the variable region of the primer. In a preferred embodiment, the melting temperature of the constant region is greater than room temperature. In a more preferred embodiment, the Tm of the constant region is greater than about 60° C., allowing the detection complex can be detected at temperatures above 60° C. Methods of generating a constant region of suitable Tm are well known in the art (see Ausubel et al., *Current Protocols In Molecular Biology*, pages 2–10.8 through 2–10.16; Figure 6.4.1, page 8.5.9 and pages 15.521–15.522, the teachings of which are incorporated herein by reference in their entirety). For example, the GC content and/or he length of the constant region can be altered, thereby altering the Tm. In one embodiment, a detection probe high in GC-content (90%) with a high melting temperature (68° C.) is used. In one embodiment the sequence of a novel FAM-labeled GC-rich detection probe is: FAM-GGGCCGGGACCGACCGCGCG (SEQ ID NO: 1). In this embodiment, the complementary sequence of the constant region of a primer is: CGCGCG-GTCGGTCCCGGCCC (SEQ ID NO: 2), wherein the variable primer sequence is attached to the 3' end of said complementary or constant sequence.

In the method of the present invention, the variable nucleic acid sequence of the primer is selected such that the primer hybridizes immediately adjacent to the polymorphism or nucleotide of interest in the nucleic acid sequence of interest. In a preferred embodiment, the primer hybridizes such that the polymorphic nucleotide or nucleotide of interest will serve as the first template nucleotide in template directed polymerization from the hybridized primer. The length of the variable region of the primer is selected such that it is at least substantially complementary to the target nucleic acid sequence, such that it allows specific hybridization between the primer and the target nucleic acid sequence within the nucleic acid sequence of interest. In the method of the present invention, the variable portion of the primer may differ in sequence from the complement of the target nucleic acid sequence so long as the target is unambiguously identified and the 3' nucleotide of the primer, which hybridizes adjacent to the polymorphism or nucleotide of interest, is complementary to the corresponding nucleotide in the target nucleic acid sequence, thus allowing the use of the method even when unanticipated polymorphisms or differences exist in the target nucleic acid sequence. One of ordinary skill in the art can readily determine, using techniques well known in the art, the necessary length of the variable region to allow specific hybridization to the target nucleic acid sequence. For example, the less complex a nucleic acid sample of interest, e.g., the shorter the sequences and/or the fewer target nucleic acid sites present, the shorter the variable region can be.

As defined herein, substantially complementary means that the variable sequence of the primer need not be the exact complementary sequence of the target nucleic acid sequence, but must be sufficiently similar in identity to the exact complement to hybridize specifically with the target nucleic acid sequence. Preferably, conditions are selected to prevent hybridization of nucleic acid sequences having more than two mismatches out of 20 continuous nucleotides and more preferably more than one mismatch out of 20 continuous nucleotides. Most preferably, the variable sequence is exactly complementary to a target nucleic acid sequence.

As used herein, the term "polymorphism" is an allelic variation in nucleic acid sequence between two or more samples. Several different types of polymorphism have been reported. A restriction fragment length polymorphism (RFLP) Is a variation in DNA sequence that alters the length of a restriction fragment (Botstein et al., *Am. J. Hum. Genet.* 32, 314–331 (1980)). The restriction fragment length polymorphism may create or delete a restriction site, thus changing the length of the restriction fragment. RFLPs have been widely used in human and animal genetic analyses (see WO 90/13668; WO90/11369; Donis-Keller, *Cell* 51, 319–337 (1987); Lander et al., *Genetics* 121, 85–99 (1989)). When a heritable trait can be linked to a particular RFLP, the presence of the RFLP in an individual can be used to predict the likelihood that the animal will also exhibit the trait.

Other polymorphisms take the form of short tandem repeats (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., FEBS Lett. 307, 113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs and VNTRs. Some single nucleotide polymorphisms (SNP) occur in protein-coding sequences (coding sequence SNP (cSNP)), in which case, one of the polymorphic forms may give rise to the expression of a defective or otherwise variant protein and, potentially, a genetic disease. Examples of genes in which polymorphisms within coding sequences give rise to genetic disease include β-globin (sickle cell anemia), apoE4 (Alzheimer's Disease), Factor V Leiden (thrombosis), and CFTR (cystic fibrosis). cSNPs can alter the codon sequence of the gene and therefore specify an alternative amino acid. Such changes are called "missense" when another amino acid is substituted, and "nonsense" when the alternative codon specifies a stop signal in protein translation. When the cSNP does not alter the amino acid specified the cSNP is called "silent".

Other single nucleotide polymorphisms occur in noncoding regions. Some of these polymorphisms may also result in defective protein expression (e.g., as a result of defective splicing). Other single nucleotide polymorphisms have no phenotypic effects.

Single nucleotide polymorphisms can be used in the same manner as RFLPs and VNTRs, but offer several advantages. Single nucleotide polymorphisms occur with greater frequency and are spaced more uniformly throughout the genome than other forms of polymorphism. The greater frequency and uniformity of single nucleotide polymorphisms means that there is a greater probability that such a polymorphism will be found in close proximity to a genetic locus of interest than would be the case for other polymorphisms. The different forms of characterized single nucleotide polymorphisms are often easier to distinguish than other types of polymorphism (e.g., by use of assays employing allele-specific hybridization probes or primers as described herein). A polymorphic nucleotide is a nucleotide that exhibits a difference between two or more individuals of the same species. The method of the present invention detects differences between two or more nucleic acid sequences manifested by at least one nucleotide difference at a specified locus within the sequence.

As used herein, a nucleotide of interest refers to a nucleotide at a particular location within a nucleic acid sequence of interest. The location can be specified in relation to the sequence complementary to the variable region of the primer. For example, it is not necessary that the sequence of the nucleic acid sequence of interest be known or that the sequence of the nucleic acid sequence of interest be known on the 3' side of the nucleotide of interest. The nucleotide of interest is the nucleotide immediately adjacent to the primer hybridized to the target nucleic acid sequence. In one embodiment, random primers are used. In a preferred embodiment, one or more target nucleic acid sequence is known and one or more primers are designed to hybridize said target nucleic acid sequence. Target nucleic acid sequence refers to that portion of the nucleic acid sequence of interest that hybridizes to the variable region of the primer immediately adjacent to the nucleotide of interest.

The nucleic acid sequence of interest can be from any number of sources. For example, the nucleic acid sequence of interest can be biologically or chemically produced. Nucleic acid sequences of interest can be of eubacterial, bacterial, viral or eukaryotic origin. Eukaryotic sources include, but are not limited to, fungal, plant, mammalian (e.g., human) and non-mammalian sources. The nucleic acid sequence of interest can be of human origin. Biological sources of material can be any tissue, biological fluid or extract that contains the nucleic acid sequence of interest. In one embodiment, the target nucleic acid sequence is specific to a genetically-based disorder or is specific to a predisposition to a genetically-based disorder. Suitable disorders can be, for example, β-Thalassemia, sickle cell anemia or Factor-V Leiden, cystic fibrosis (CF), or cancer-related genes such as p53 and pTEN, or BRC-1 and BRC-2 for breast cancer susceptibility. In yet another embodiment, isolated chromosomal DNA may be investigated for paternity testing, identity confirmation or other forensic purpose. The nucleic acid sequence of interest can be specific for a pathogen or a microorganism; for example, the nucleic acid sequence of interest can be from a virus, bacterium, fungus, parasite or a yeast.

Nucleic acid sequences of interest can be produced as a result of a transcription reaction. In another embodiment, the nucleic acid sequence of interest can be produced as a result of an amplification reaction; for example, the amplification reaction can be polymerase chain reaction (PCR), ligase chain reaction (LCR), strand displacement amplification (SDA), transcription mediated amplification (TMA), Qβ-replicase amplification (Q-beta) or rolling circle amplification (RCA). The nucleic acid sequence of interest can be DNA or RNA.

In another embodiment, PCR products can be detected by the method of the present invention. In this embodiment, the nucleotide of interest is the nucleic acid amplified in the PCR reaction. In this embodiment, the variable region of the primer is designed to hybridize the amplified nucleic acid of interest, if present, in the PCR reaction. This method can detect the presence and/or quantity of the nucleic acid of interest. In this embodiment, the PCR sample can be analyzed in the reaction vessel, or a portion of the PCR reaction can be removed to a separate vessel, or all or a portion of the PCR reaction can be immobilized on a solid support as described below.

As demonstrated in the Exemplification, the present invention allows the detection and/or identification of polymorphisms or nucleotides of interest in a single tube or reaction vessel, without washing or removal of non-hybridized probes, primers or unincorporated labeled nucleotides. However, the methods of the present invention also include embodiments that include washing or removal steps. Such washing or removal steps can affect specificity of hybridization due to increased or decreased stringency of said steps. In one embodiment, washing or removal steps can be useful when the donor and acceptor fluorescent molecules are the same. In this embodiment, the excitation light is polarized and emission of unpolarized light is indicative of fluorescence resonance energy transfer.

In another embodiment of the present invention, the SBE can be conducted with one or more primers and one or more nucleic acids of interest, followed by hybridization of the extended primers to detection probes. In this embodiment, the detection probes may be free in solution or immobilized on a solid support.

The skilled artisan will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. Optimal stringency for an assay may be experimentally determined by examining variations of each stringency factor until the desired degree of discrimination between the variable region and target sequences has been achieved. The level of assay stringency will increase or decrease depending on whether the target and variable regions are complementary or substantially complementary.

A general description of stringent hybridization conditions is provided in Ausubel, F. M., et al., *Current Protocols in Molecular Biology*, Greene Publishing Assoc. and Wiley-Interscience 1989, the teachings of which are incorporated herein by reference. The influence of factors such as probe length, base composition, percent mismatch between the hybridizing sequences, temperature and ionic strength on the stability of nucleic acid hybrids is well known in the art. Thus, stringency conditions sufficient to allow the primers of the present invention to hybridize with specificity to a target nucleic acid sequence can be determined empirically. As described above, the primers need not hybridize to the nucleic acid sequence of interest with exact complementarity, so long as the target nucleic acid sequence of interest is unambiguously hybridized. Similarly, appropriate conditions for hybridization of the detection probe to the primer can be readily determined by the skilled artisan. Conditions for stringency are also described in: Secreted Proteins and Polynucleotides Encoding Them, (Jacobs et al., WO 98/40404), the teachings of which are incorporated herein by reference. In particular, examples of highly stringent, stringent, reduced and least stringent conditions are provided in WO 98/40404 in the Table on page 36. In one embodiment of the present invention, highly stringent conditions are those that are at least as stringent as, for example, 1×SSC at 65° C., or 1×SSC and 50% formamide at 42° C. Moderate stringency conditions are those that are at least as stringent as 4×SSC at 65° C., or 4×SSC and 50% formamide at 42° C. Reduced stringency conditions are those that are at least as stringent as 4×SSC at 50° C., or 6×SSC and 50% formamide at 40° C.

According to the method of the present invention, the variable region of the primer hybridizes to the target nucleic acid sequence immediately adjacent to the polymorphic nucleotide or nucleotide of interest, such that the primer can be used to prime template-dependent synthesis of a nucleic acid molecule, wherein a nucleotide, complementary to a polymorphic nucleotide or nucleotide of interest and labeled with an acceptor fluorescent molecule, is added to the primer. In one embodiment of the present invention, template-dependent synthesis is conducted using a thermostable polymerase following a thermocycling protocol. Any suitable thermostable polymerase can be used in the present invention, including, but not limited to, pfu®, taq®, Amplitaq® or Vent®. Furthermore, non-thermostable polymerases can be used, provided conditions are chosen such that sufficient extension occurs. Such conditions include, but are not limited to, augmenting the reaction with additional polymerase, reducing the reaction temperature or performing of a single round of extension. In one embodiment, less than about 30 rounds of thermocycling are performed. In a preferred embodiment, 6 rounds of thermocycling are performed. It is understood that the number of cycles is reduced with increasing specific activity of the detection complex, or with increasing sensitivity of the detection apparatus such that sufficient signal is generated. For example, a charge-coupled device can be used to detect FRET, thereby increasing the detection sensitivity.

The primers and probes can be combined with the nucleic acid sequence of interest simultaneously or sequentially. Furthermore, one or more blocking nucleic acid sequences may be used to reduce binding of the primers and probes to non-target sequences. Blocking nucleic acid sequences are PNA, RNA or DNA sequences or combinations thereof which are used to suppress the binding of the primer to a site which is unrelated to the target sequence. While not wishing to be bound by theory, it is believed that the blocking sequences suppress the binding of the primer to non-target sequences because the blocking sequences hybridize to the non-target sequence.

In the present invention, donor and acceptor molecules operate in a set wherein one or more acceptor molecules accepts energy from one or more donor molecules, or otherwise quenches signal from the donor molecule, when the donor and acceptor molecules are closely associated. In one embodiment, the donor and acceptor molecules are about 30 to about 200 Å apart or about 10 to about 40 nucleotides apart. Transfer of energy may occur through collision of the closely associated molecules of a set, or through a non-radiative process such as fluorescence resonance energy transfer (FRET). For FRET to occur, transfer of energy between donor and acceptor molecules requires that the molecules be close in space and that the emission spectrum of a donor have substantial overlap with the absorption spectrum of the acceptor (Yaron et al. *Analytical Biochemistry*, 95, 228–235 (1979), the teachings of which are incorporated herein by reference in their entirety). Alternatively, intramolecular energy transfer may occur between very closely associated donor and acceptor molecules (e.g., within 10 Å) whether or not the emission spectrum of a donor molecule has a substantial overlap with the absorption spectrum of the acceptor molecule (Yaron et al.) This process is referred to as intramolecular collision since it is believed that quenching is caused by the direct contact of the donor and acceptor molecule (Yaron et al.).

Because the efficiency of both collision and non-radiative transfer of energy between the donor and acceptor molecules is directly dependent on the proximity of the donor and acceptor molecules, formation and dissociation of the complexes of this invention can be monitored by measuring at least one physical property of at least one member of the set which is detectably different when the complex is formed, as compared with when the nucleotide primers and probes exist independently and unassociated. Preferably, the means of detection will involve measuring fluorescence of an acceptor fluorophore of a set or the fluorescence of the donor fluorophore in a set containing a fluorophore and quencher pair (e.g. a donor and acceptor). While not wishing to be bound by theory, the fluorescent molecules may interact with one another via hydrophobic interactions, thereby reducing the adverse effect of distance between the donor and acceptor fluorescent molecules. Thus, fluorescence energy transfer can occur when the donor and acceptor fluorescent molecules are up to about 40 nucleotides away from each other. In one embodiment, the detection complex comprising the primer extend by an acceptor-labeled nucleotide and the detection probe is no longer hybridized to the target nucleic acid sequence when acceptor molecule fluorescence is measured. In a preferred embodiment, the acceptor molecule fluorescence is measured at a temperature above the Tm of the variable region.

In one embodiment of the present invention, the ddNTP corresponding to the complement of one possible nucleotide present at the polymorphic locus is labeled with N, $N_1$, N, $N^1$-tetramethyl-6-carboxy rhodamine (TAMRA) and the complement of another possible nucleotide present at the polymorphic locus is labeled with 6-carboxy-X-rhodamine (ROX), (see Example 2). Depending on the identity of said polymorphism or nucleotide of interest, the FRET primer is extended with a ROX-labeled or TAMRA-labeled ddNTP. Upon incorporation of either ROX- or TAMRA-labeled ddNTP, energy transfer occurs between the donor dye (FAM) of the detector probe and the acceptor dye (the ROX- or TAMRA-attached to the ddNTP). Donor and acceptor molecules suitable for FRET are well known in the art (see page 46 of R. P. Haugland, Handbook of Fluorescent Probes and Research Chemicals, 6th ed.; Molecular Probes, Oregon, the teachings of which are incorporated herein by reference). Typically, to obtain fluorescence resonance energy transfer, the donor fluorescent molecule has a shorter excitation wavelength than the acceptor fluorescent molecule and the donor emission wavelength overlaps with the acceptor excitation wavelength, to allow transfer of energy from the donor to the acceptor. Preferred fluorophores are fluorescein and derivatives thereof, such as 5-(2'-aminoethyl)-aminoapthalene-1-sulfonic acid (EDANS) and rhodamine and derivatives thereof such as Cy3, Cy5 and Texas Red. Suitable donor/acceptor pairs are, for example, fluorescein/tetramethyrhodamine, IAEDANS/fluorescein and EDANS/DABCYL. In another embodiment of the present invention, the same fluorescent molecule is used for the donor and acceptor. In this embodiment, the wavelength used to excite the detection complexes is polarized. Unpolarized emission detected is indicative of FRET. In this embodiment, it is preferable to remove unincorporated labeled nucleotides (e.g., by washing) to improve the detection signal.

Those of ordinary skill in the art will recognize that labeled, unlabeled and modified nucleotides are readily available for the method of the present invention. They can be synthesized using commercially available instrumentation and reagents or they can be purchased from numerous commercial vendors of custom manufactured oligonucleotides.

The method of the present invention can be used to analyze more than one polymorphic nucleotide or nucleotide of interest in a given nucleic acid sequence of interest. Furthermore, the present invention can be used to analyze multiple nucleic acid sequences for one or more polymorphic nucleotides or nucleotides of interest. These embodiments are referred to herein as multiplex analysis. For example, a single polynucleic acid of interest can be analyzed at two or more loci. In this example, primers are used such that the variable region of each primer is distinct and hybridizes to unique target nucleic acid sequence (specific locus of interest). In one embodiment, each primer can have a unique constant region, such that a detection probe specific for each primer and labeled with a distinguishable donor fluorescent molecule is used. Thus, the nucleotide of interest at each locus is analyzed by interrogation at different excitation wavelengths, wherein each wavelength is specific for a donor molecule. Detection is measured at the acceptor emission wavelength. The same set of acceptor labeled nucleotides can be used for each locus. In another embodiment, the same detector fluorescent molecule can be used for each locus. In one embodiment, a positive read-out is obtained when either locus is detected in the sequence of interest. In another embodiment, the set of donor and acceptor molecules can be chosen such that a unique readout is obtained for each locus, wherein the readout is defined by the excitation and emission wavelength.

The present invention further provides a method to diagnose a genetically-based disorder or predisposition for a genetically-based disorder, wherein two or more nucleotides of interest are related to each other and wherein detection of any one of said nucleotides is useful or necessary to the proper diagnosis. In one embodiment, the nucleotides of interest can have similar sequence. For example, the present invention can be used to detect any number of mutations in the α-globin gene cluster or in the β-globin gene cluster, where any one of said mutations results in Thalassemia. In another embodiment, the nucleotide sequences of interest do not share sequence similarity, yet presence of any one of the sequences can be used to diagnose disease or predisposition to disease. For example, genes linked to a predisposition in Alzheimer's disease such as ApoE, bleomycin hydrolase or β-amyloid precursor protein can be analyzed for alterations associated with Alzeheimer's disease. In this embodiment of detecting any one or two or more sequences of interest, at least two probe sets are used, such that the variable region of the first and second primers of each set are distinct. Said probe sets hybridize to unique target nucleic acid sites. In this embodiment, the FRET readout or acceptor molecule emission of all complexes can be the same regardless of the nature of the unique target nucleic acid sequence to which they are bound. Thus, the presence of any one of a group of target nucleic acid sequence in a sample will result in the generation of a positive signal. In this embodiment, the same detection probe can be used. Examples of such diseases and conditions of clinical interest have been previously described.

The present invention can be used to analyze one or more polymorphic nucleotides, one or more nucleotides of interest and combinations thereof. In one embodiment of the present invention, the different polymorphisms or nucleotides of interest analyzed in the single reaction are distinguishable. In one embodiment, different sets of donor and acceptor fluorescent molecules are used to distinguish the different nucleotides of interest. For example, detection probes can comprise donor fluorescent molecules of different excitation wavelengths and distinct detection sequences. In this embodiment, one target-specific primer has a constant region that hybridizes to one detector probe, and a primer specific for another target sequence has a constant region complementary to a second detector probe. In this embodiment, the same acceptor molecule labeled nucleotides can be used, and detection is conducted at separate excitation wavelengths. It is understood that any combination of donor and acceptor molecules with different detection sequences can be used to distinguish the nucleotides of interest on one or more polynucleic acid of interest.

In another embodiment of multiplexing, either the detector probes, primers or polynucleic acids of interest can be immobilized onto a solid support. Immobilization of any of these components, allows a layer of multiplexing in addition to the use of different donor/acceptor molecule pairs and detection sequences as described above. For example, the different detector probes can be immobilized on a solid support at defined locations. In this embodiment, primers having a constant region that is complementary to an immobilized detection probe are used. In one embodiment, multiple primers can be used in solution with polynucleic acid of interest followed by hybridization of the extended primers to the immobilized detection probes. In another embodiment, the primers can be hybridized to the detection probes before SBE. Multiple nucleotides of interest can be analyzed simultaneously in the same tube or vessel, where "vessel" includes any suitable solid support such as wells, slides, chips or beads. Each nucleotide of interest is distinguished by its location on the solid support as well as the FRET read-out, thus, the same detector/acceptor pairs can be used for each nucleotide of interest. Following the formation of detection complexes and detection of said complexes, the immobilized detection probe can optionally be reused after removal of hybridized primer or hybridized primer/target nucleic acid sequence complex.

In another example of the present invention, the primers are immobilized on a solid support. In this embodiment, primers having variable regions complementary to different target nucleic acid sequences are used. In this embodiment, the detection probe can be added before or after SBE. Multiple nucleotides of interest can be analyzed simultaneously in the same tube or vessel. If more than one target site is being analyzed, the primers can be mutually distinguishable. In one embodiment, the primers are immobilized at known locations. In another embodiment, the primers have distinguishable constant regions.

In another embodiment of the present invention, nucleic acid sequences of interest comprising various target sites are immobilized on a solid support at defined locations. In still another embodiment, a given immobilized nucleic acid sequence of interest can be analyzed for more than one polymorphism or nucleotide of interest at more than one target site within the nucleic acid of interest. In this embodiment, the detection probe and acceptor molecule pairs can be selected to detect each of the polymorphic nucleotides or nucleotides of interest separately, or to detect any one of the polymorphic nucleotides or nucleotides of interest.

The multiplex analysis of the present invention can be further extended to chips or arrays. As used herein, arrays are surfaces on which two or more detection complexes have been formed, each detection complex at a specified position. Because the location and composition of each detection complex is known, arrays are generally used to simultaneously detect, identify or quantitate two or more target nucleic acid sequences in the sample. Thus, arrays of detection complexes may be useful in diagnostic applications or in screening compounds.

For example, an array of unique support-bound detection probes or primers could be manufactured, wherein each support-bound detection probe or primer exists at a known location on the array. Each support-bound detection probe or primer would be suitable for the detection or quantitation of one of several unique target nucleic acid sequences which might be present in a sample. The sample of interest is contacted with the support in the presence of a mixture of primer or detection probes and acceptor-labeled nucleotides, under conditions suitable for the formation of detection complexes at a position on the array. In one embodiment, the primers are immobilized and suitable detection probes are added. In another embodiment, detection probes are immobilized and suitable primers are added. Suitable probes, for example have detection sequences complimentary to the constant region of the primer. Suitable primers, for example have a constant region complimentary to the immobilized detection probe and a variable region complimentary to the target nucleic acid sequence. Thus, the presence or identity of at least one target nucleic acid sequence can be correlated with the presence of detectable FRET signal at a defined location on the array. In one embodiment, a common detection probe is used. For example, the same detection probe can be used to generate signal at any position on the array where a primer has been extended.

The present invention further comprises primer/probe sets comprising a target-specific primer and a detection probe, wherein said primer comprises a variable region and a constant region, such that the variable region is complementary to a target nucleic acid sequence immediately adjacent to the polymorphic nucleotide or target nucleotide of interest and wherein the constant region is complementary to the detection sequence of the detection probe, wherein the detection probe is labeled with a donor fluorescent molecule. In one embodiment, the detection sequence comprises a G/C rich sequence. In another embodiment, the detection sequence comprises SEQ ID NO: 1. In yet another embodiment the constant region of said primer comprises SEQ ID NO: 2.

Furthermore, the present invention comprises kits suitable for detection of polymorphisms or nucleotides of interest. The kits of the present invention comprise at least one detection probe comprising a detection sequence, wherein said detection probe is labeled with a donor fluorescent molecule. The kit can further comprise a primer, wherein said primer comprises a variable region and a constant region, such that the variable region hybridizes under appropriate conditions immediately adjacent to a polymorphism a nucleic acid sequence of interest. The constant region of the primer hybridizes to said detection probe. The kit can further comprise dideoxynucleotides labeled with fluorescent acceptor molecules.

The invention will be further illustrated by the following non-limiting examples. The teachings of all references cited herein are incorporated herein by reference in their entirety.

EXAMPLES

Example 1

Amplification of the Nucleic Acid Sequence of Interest

The locus of interest was amplified using polymerase chain reaction.

First, a PCR mix was prepared following the recipe below:

PCR Mix:

|  | Each Reaction ($\mu$L) | For 96-well Plate ($\mu$L) |
|---|---|---|
| 10 mM dNTP | 0.15 | 16.2 |
| 25 mM MgCl$_2$ | 0.9 | 97.2 |
| 10X Taq Buffer | 1.5 | 162.0 |
| 1 $\mu$M PCR Primer Mix | 2.5 | 270.0 |
| ddH$_2$O | 4.8 | 518.4 |
| 5 U/$\mu$l Amplitaq-gold ® | 0.15 | 16.2 |
|  | 10 | 1080 |

Ten microliters of PCR mix were added to 5 $\mu$L genomic DNA (5 ng/$\mu$L), and the plate was sealed with MJ plate-seal 'A'.

PCR was conducted using the following program:

96° C. for 10 minutes

96° C. for 30 seconds, 50° C. for 1 minute, 72° C. for 1 minute, for 35 cycles;

72° C. for 10 minutes followed by a hold at 4° C.

The PCR product was treated with alkaline phosphatase and exonuclease I (ExoI). In the same PCR plate, PCR products were spun down. An alkaline phosphatase/exonuclease mix was prepared and according to the following recipe.

|  | Each reaction (μL) | For 96-well plate (μL) |
|---|---|---|
| Shrimp alkaline phosphatase (1 U/μl) | 0.5 | 52 |
| Exonuclease I (10 U/μl) | 0.1 | 10.4 |
| 10X SAP buffer | 2.0 | 208 |
| ddH₂O | 2.4 | 249.6 |
|  | 5.0 | 520 |

Five microliters of SAP/EXO mix were added to 15 μL PCR product and the plate was sealed with Microseal A film. The mixture was incubated at 37° C. for 45 minutes and then at 96° C. for 15 minutes.

Example 2

Single-Base Extension/Fluorescence Detection in AB 17700 26

A SBE-FRET mix was prepared following the receipe below:

|  | Each reaction (μL) | For 96-well plate (μL) |
|---|---|---|
| GC-FAM primer (1 μM) | 4.0 | 416 |
| ROX ddNTP (1 μM) | 2.0 | 208 |
| (ROX labeled reference) TAMRA ddNTP (1 μM) (TAMRA base) | 2.0 | 208 |
| SBE-PRIMER (20 μM) | 2.0 | 208 |
| Thermoseq. Buffer (10X) | 2.0 | 208 |
| ddH₂O | 4.975 | 517.4 |
| Thermosequenase (20 U/μL) | 0.025 | 2.6 |
|  | 13.0 | 1352 |

Thirteen microliters of SBE-FRET mix were added to MJ 0.2 mL polypropylene plates. Seven microliters of SAP/EXO-treated PCR products was added to SBE-FRET mix on MJ plates and mixed by tapping on bench and spinning briefly if necessary. The wells were capped with optical caps and rolled with roller if necessary. The plates were placed in ABI7700 and incubated for 6 cycles of (for a 20 μL reaction):

96° C. for 15 seconds,

50° C. for 30 seconds,

60° C. for 30 seconds, and data was collected at 60° C.

Figure 2A:
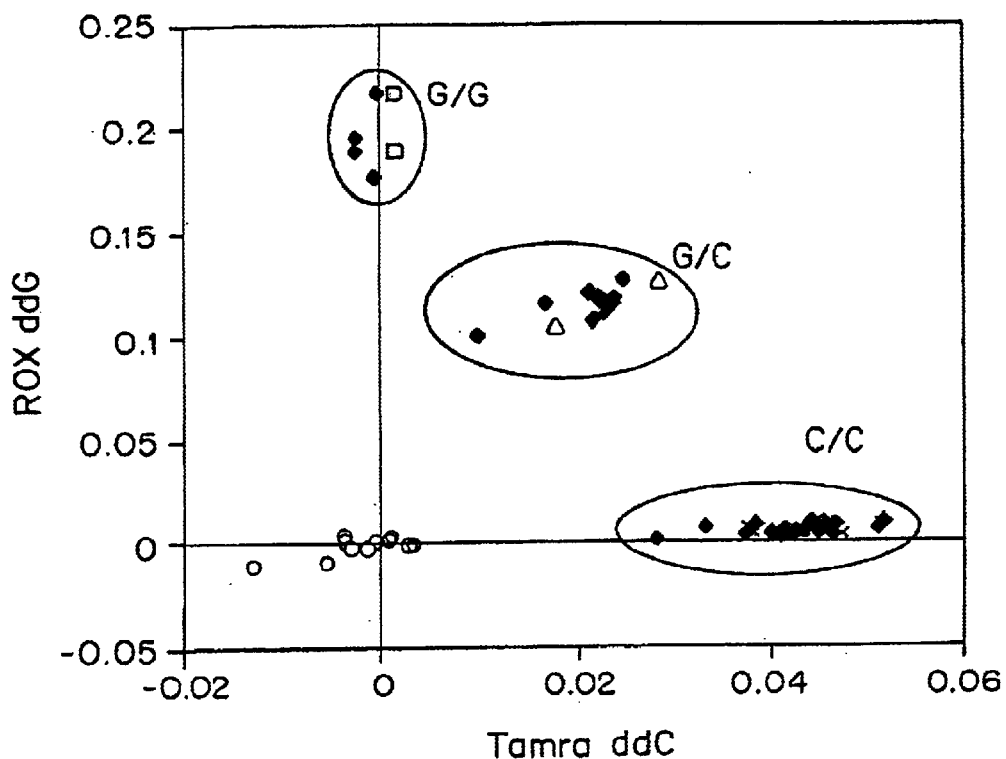
FIG. 2A is a scatter plot of the results of G/C polymorphism identification in F13A1u4 (TGTGACAGTTSAGTTTACCAA, SEQ ID NO: 3) using a FAM-labeled FRET primer according to traditional SBE/FRET protocols.
Figure 2B:
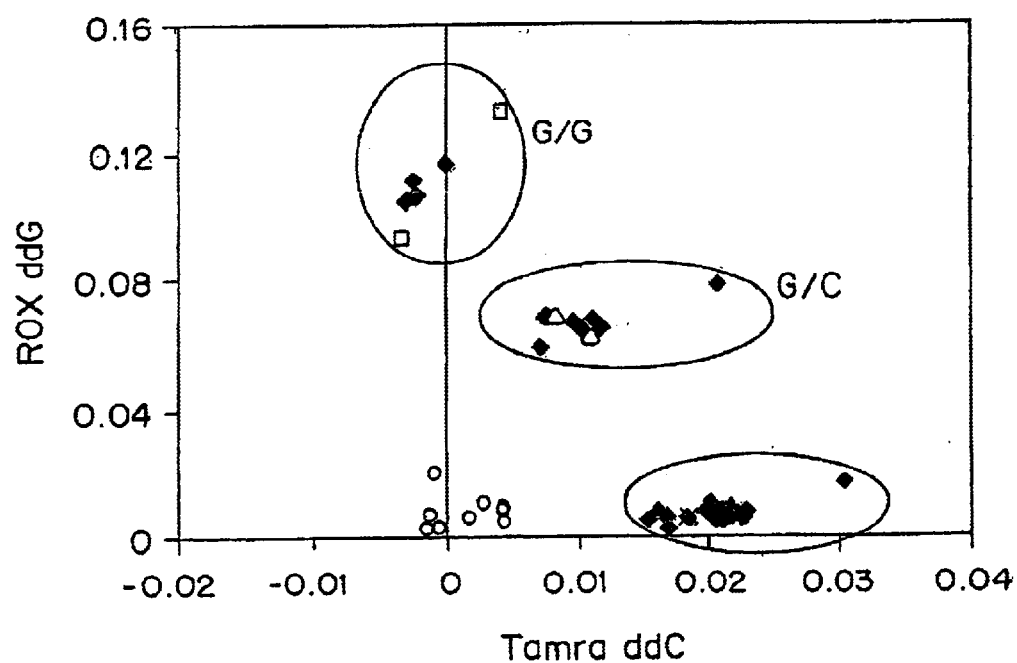
FIG. 2B is a scatter plot of the results of G/C polymorphism identification in F13A1u4 (SEQ ID NO: 3) using the method of the present invention.

FIG. 2 shows the results of analysis of a polymorphic site in locus F13Alu4 (SEQ ID NO: 3) wherein the nucleotide of interest is G or C. FIG. 2a shows the results from conventional SBE/FRET where the target specific primer is labeled with both the donor and acceptor molecules. FIG. 2b shows the results from the method of the present invention, using a generic detection probe.

Figure 3A:
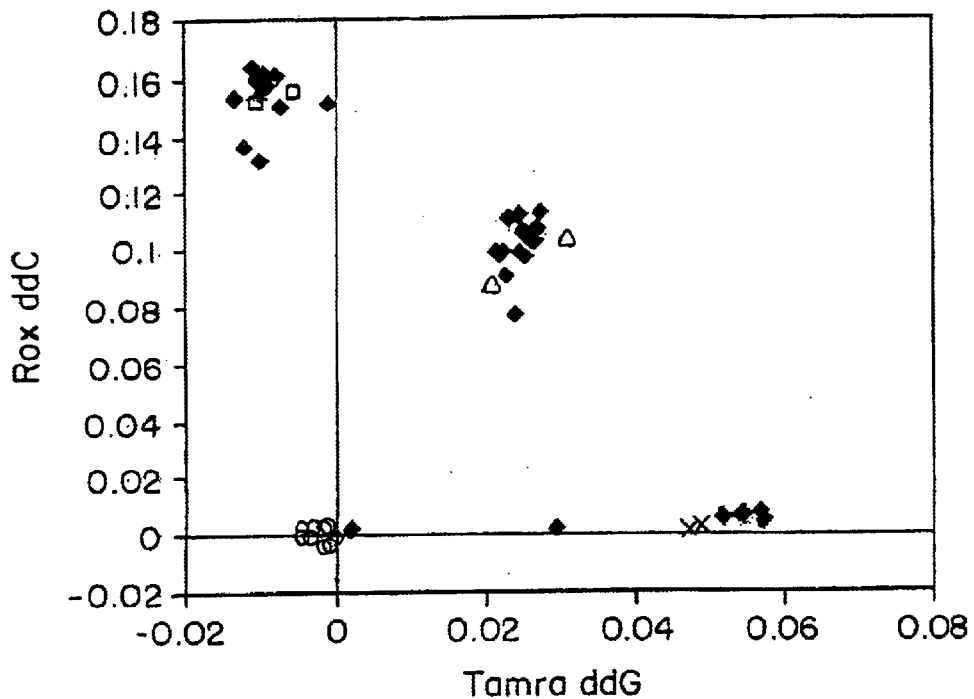
FIG. 3A is a scatter plot of the results of G/C polymorphism identification in PAI2u4 (AGATAACCAASTGCATTTTAT, SEQ ID NO: 4) using a FAM-labeled FRET primer according to traditional SBE/FRET protocols.
Figure 3B:
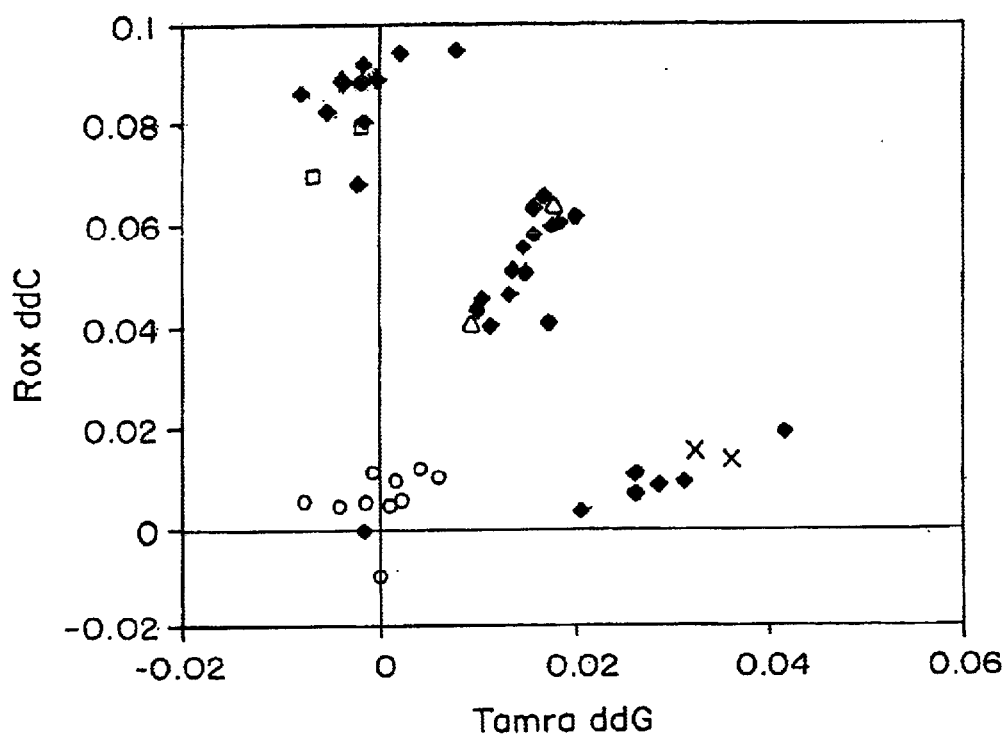
FIG. 3B is a scatter plot of the results of G/C polymorphism identification in PAI2u4 (SEQ ID NO: 4) using the method of the present invention.
Figure 4A:
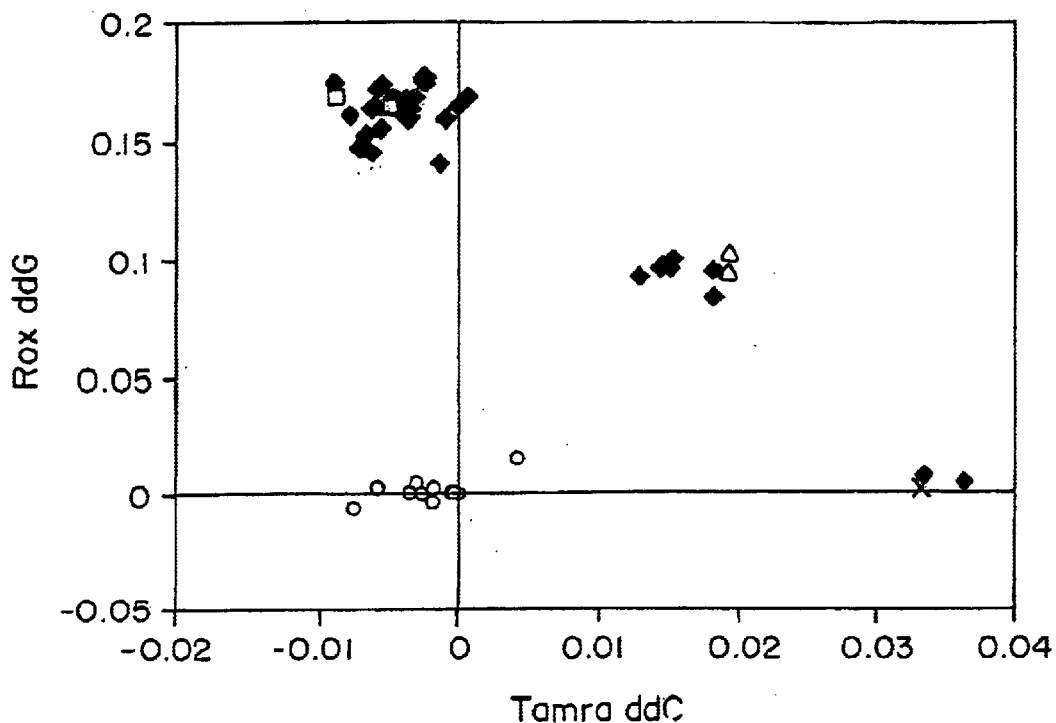
FIG. 4A is a scatter plot of the results of G/C polymorphism identification in F5u18 (AAATAAGGCASATAAGCCCTT, SEQ ID NO: 5) using a FAM-labeled FRET primer according to traditional SBE/FRET protocols.
Figure 4B:
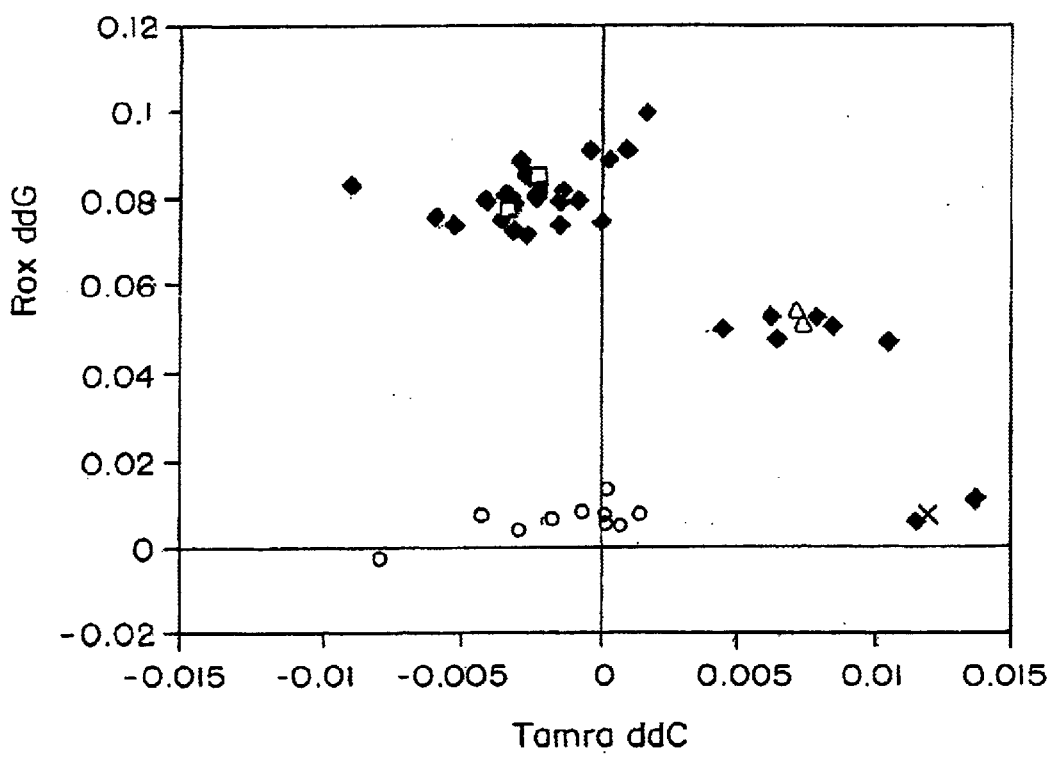
FIG. 4B is a scatter plot of the results of G/C polymorphism identification in F5u18 (SEQ ID NO: 5) using the method of the present invention.
Figure 5A:
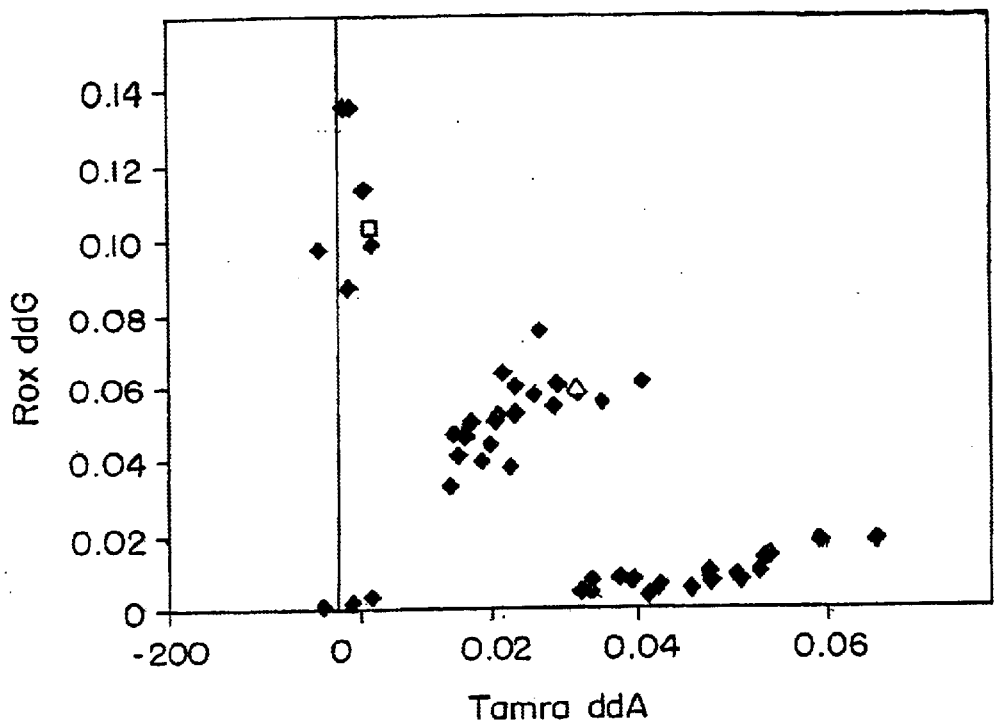
FIG. 5A is a scatter plot of the results of G/A polymorphism identification in F5u36 (CAACATGCCTRTGGACATGAG, SEQ ID NO: 6) using a FAM-labeled FRET primer according to traditional SBE/FRET protocols.
Figure 5B:
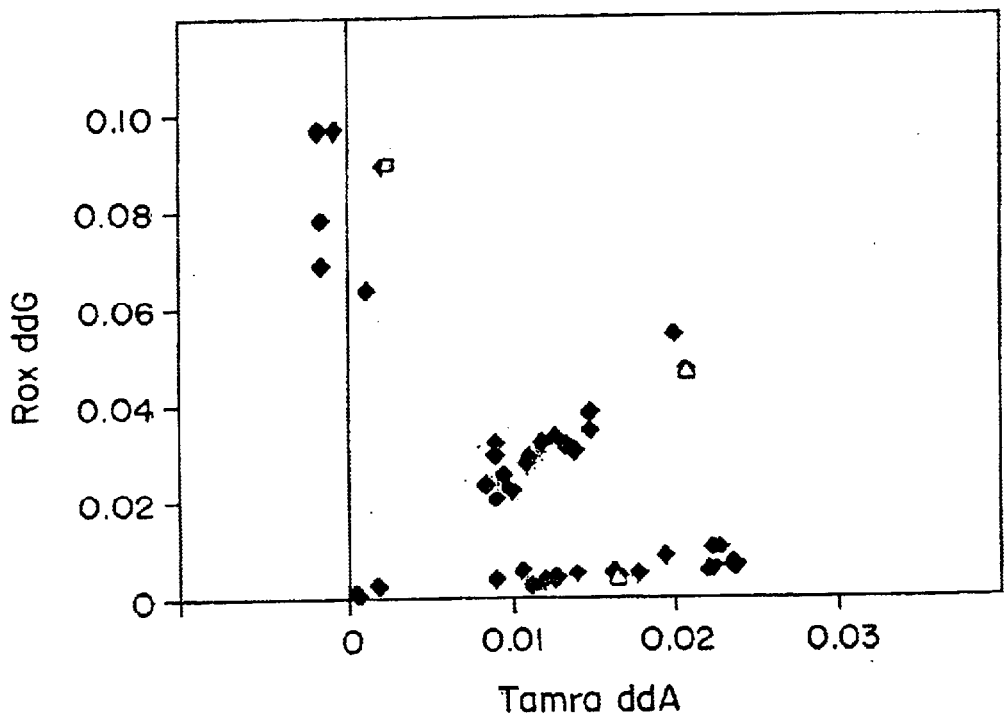
FIG. 5B is a scatter plot of the results of G/A polymorphism identification in F5u36 (SEQ ID NO: 6) using the method of the present invention.

FIGS. 3–5 show similar analyses at different loci, in particular at PAI2U4, F5U18 and F5U36, respectively.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining the identity of one or more nucleotides of interest in at least one nucleic acid sequence of interest comprising the steps of;
   a) combining
      i) a nucleic acid sequence of interest having at least one nucleotide of interest,
      ii) a detection probe comprising a detection sequence and a donor fluorescent molecule,
      iii) a primer comprising a variable nucleic acid sequence which hybridizes to said nucleic acid sequence of interest immediately adjacent to said nucleotide of interest, and a constant region comprising a nucleic acid sequence complementary to said detection sequence of the detection probe, and
      iv) one or more dideoxynucleotides labeled with an acceptor fluorescent molecule, under conditions suitable for template-dependent single base extension of said primer, wherein one of said dideoxynucleotides is added to said primer by template-directed extension, thereby forming a detection. complex comprising a primer extended by one labeled dideoxynucleotide and a detection probe, wherein the detection probe is hybridized to the constant region of said extended primer; and
   b) detecting the detection complex of a), thereby determining the identity of one or more nucleotides of interest in at least one nucleic acid sequence of interest.

2. The method of claim 1, wherein the detection complex is detected by fluoresence resonance energy transfer.

3. The method of claim 1 wherein the dideoxynucleotide labeled with an acceptor fluorescent molecule is added to said primer using a thermostable polymerase and a suitable thermocycling program.

4. The method of claim 1, wherein the nucleic acid sequence of interest is produced chemically or enzymatically, or is isolated from a source of interest.

5. The method of claim 4, wherein the nucleic acid sequence of interest is produced by polymerase chain reaction.

6. The method of claim 1, wherein the nucleic acid sequence of interest is immobilized on a solid support.

7. The method of claim 6, wherein the nucleic acid sequence of interest is immobilized at defined locations of the solid support.

8. The method of claim 1, wherein the primer is from about 10 to about 110 nucleotides in length.

9. The method of claim 8, wherein the primer is from about 30 to about 60 nucleotides in length.

10. The method of claim 9, wherein the constant region of said primer comprises a guanine/cytosine-rich sequence.

11. The method of claim 10, wherein the constant region comprises SEQ ID NO: 2.

12. The method of claim 1, wherein the detection sequence is from about 6 to about nucleotides in length.

13. The method of claim 12, wherein the detection sequence is from about 10 to about 40 nucleotides in length.

14. The method of claim 13, wherein the detection sequence comprises a guanine/cytosine-rich sequence.

15. The method of claim 14, wherein the detection sequence comprises SEQ ID NO. 1.

16. The method of claim 1, wherein the primer is immobilized on a solid support.

17. The method of claim 16 wherein the primer is immobilized on a solid support at defined locations.

18. The method of claim 1, wherein the detection probe is immobilized on a solid support.

19. The method of claim 18, wherein the detection probe is immobilized on a solid support at defined locations.

20. The method of claim 1, wherein the donor fluorescent molecule is selected from the group consisting of: fluorescein, IAEDANS, EDANS, TAMRA, DABCYL, 6-carboxy-X-rhodamine, Cy3, Cy5 and Texas Red.

21. The method of claim 1, wherein the acceptor fluorescent molecule is selected from the group consisting of: TAMRA, fluorescein, DABCYL, 6-carboxyl-X-rhodamine, IAEDANS, EDANS, Cy3, Cy5 and Texas Red.

22. A method of determining the identity of one or more nucleotides of interest in more than one nucleic acid sequence of interest, comprising the steps of;
  a) combining
    i) more than one nucleic acid sequence of interest, each having at least one nucleotide of interest,
    ii) a detection probe comprising a detection sequence and a donor fluorescent molecule,
    iii) one or more primers comprising a variable nucleic acid sequence which hybridizes to one of said nucleic acid-sequences of interest immediately adjacent to a nucleotide of interest and a constant region comprising a nucleic acid sequence complementary to said detection sequence of the detection probe, and
    iv) one or more dideoxynucleotides labeled with an acceptor fluorescent molecule, under conditions suitable for template-dependent single base extension of said primers, wherein said acceptor fluorescent molecule-labeled dideoxynucleotides are added to said primers by template-directed extension, thereby forming one or more detection complexes comprising a primer extended by one labeled dideoxynucleotide and a detection probe, wherein the detection probe is hybridized to the constant region of said extended primer; and
  b) detecting one or more of said detection complexes of a), thereby determining the identity of one or more nucleotides of interest in at least one nucleic acid sequence of interest.

23. The method of claim 22, wherein the detection complex is detected by fluoresence resonance energy transfer.

24. The method of claim 22 wherein the dideoxynucleotides are added to said primer using a thermostable polymerase and a suitable thermocycling program.

25. The method of claim 22, wherein the nucleic acid sequence of interest is produced chemically, enzymatically, or isolated from a source of interest.

26. The method of claim 25, wherein the nucleic acid sequence of interest is produced by polymerase chain reaction.

27. The method of claim 22, wherein the nucleic acid sequence of interest is immobilized on a solid support.

28. The method of claim 27, wherein the nucleic acid sequence of interest is immobilized at defined locations of the solid support.

29. The method of claim 22, wherein the primer is from about 10 to about 110 nucleotides in length.

30. The method of claim 29, wherein the primer is from about 30 to about 60 nucleotides in length.

31. The method of claim 30, wherein the constant region of said primer comprises a guanine/cytosine-rich sequence.

32. The method of claim 31, wherein the constant region comprises SEQ ID NO: 2.

33. The method of claim 22, wherein the detection sequence is from about 6 to about 60 nucleotides in length.

34. The method of claim 33, wherein the detection sequence is from about 10 to about 40 nucleotides in length.

35. The method of claim 34, wherein the detection sequence comprises a guanine/cytosine-rich sequence.

36. The method of claim 35, wherein the detection sequence comprises SEQ ID NO: 1.

37. The method of claim 36, wherein the primer is immobilized on a solid support.

38. The method of claim 22 wherein the primer is immobilized on a solid support at defined locations.

39. The method of claim 38, wherein the detectable probe is immobilized on a solid support.

40. The method of claim 22, wherein the donor fluorescent molecule is selected from the group consisting of: fluorescein, IAEDANS, EDANS, TAMRA, DABCYL, 6-carboxy-X-rhodamine, Cy3, Cy5 and Texas Red.

41. The method of claim 22, wherein the acceptor fluorescent molecule is selected from the group consisting of: TAMRA, fluorescein, DABCYL, 6-carboxyl-X-rhodamine, IAEDANS, EDANS, Cy3, Cy5 and Texas Red.

42. A method of determining the identity of one or more nucleotides of interest in at least one nucleic acid sequence of interest comprising the steps of;
  a) combining
    i) a nucleic acid sequence of interest having at least one nucleotide of interest,
    ii) a detection probe comprising a detection sequence and a donor fluorescent molecule,
    iii) a primer comprising a variable nucleic acid sequence which hybridizes to said nucleic acid sequence of interest immediately adjacent to said nucleotide of interest, and a constant region comprising a guanine/cytosine-rich nucleic acid sequence complementary to said detection sequence of the detection probe, wherein the constant region comprises SEQ ID NO: 2, and wherein the primer is from about 30 to about 60 nucleotides in length, and
    iv) one or more dideoxynucleotides labeled with an acceptor fluorescent molecule, under conditions suitable for template-dependent single base extension of said primer, wherein said dideoxynucleotide is added to said primer by template-directed extension, thereby forming a detection complex; and
  b) detecting the detection complex of a).

43. A method of determining the identity of one or more nucleotides of interest in at least one nucleic acid sequence of interest comprising the steps of;
  a) combining
    i) a nucleic acid sequence of interest having at least one nucleotide of interest, ii) a detection probe comprising a guanine/cytosine-rich detection sequence and a donor fluorescent molecule, wherein the detection sequence is from about 10 to about 40 nucleotides in length and wherein the detection sequence comprises SEQ ID NO: 1, iii) a primer comprising a variable nucleic acid sequence which hybridizes to said nucleic acid sequence of interest immediately adjacent to said nucleotide of interest, and a constant region comprising a nucleic acid sequence complementary to said detection sequence of the detection probe, and iv) one or more dideoxynucleotides labeled with an acceptor fluorescent molecule, under conditions suitable for template-dependent single base extension of said primer, wherein said dideoxynucleotide is added to said primer by template-directed extension, thereby forming a detection complex; and b) detecting the detection complex of a).

44. A method of determining the identity of one or more nucleotides of interest in more than one nucleic acid sequence of interest, comprising the steps of;

a) combining
i) more than one nucleic acid sequence of interest, each having at least one nucleotide of interest,
ii) a detection probe comprising a detection sequence and a donor fluorescent molecule,
iii) one or more primers comprising a variable nucleic acid sequence which hybridizes to one of said nucleic acid sequences of interest immediately adjacent to a nucleotide of interest and a constant region comprising a guanine/cytosine-rich nucleic acid sequence complementary to said detection sequence of the detection probe, wherein the constant region comprises SEQ ID NO: 2 and wherein the primers are from about 30 to about 60 nucleotides in length, and
iv) one or more dideoxynucleotides labeled with an acceptor fluorescent molecule, under conditions suitable for template-dependent single base extension of said primers, wherein said acceptor fluorescent molecule-labeled dideoxynucleotides are added to said primers, by template-directed extension, thereby forming one or more detection complexes;

b) detecting one or more of said detection complexes of a).

45. A method of determining the identity of one or more nucleotides of interest in more than one nucleic acid sequence of interest, comprising the steps of;

a) combining
i) more than one nucleic acid sequence of interest, each having at least one nucleotide of interest,
ii) a detection probe comprising a guanine/cytosine-rich detection sequence and a donor fluorescent molecule, wherein the detection sequence is from about 10 to about 40 nucleotides in length and wherein the detection sequence comprises SEQ ID NO: 1,
iii) one or more primers comprising a variable nucleic acid sequence which hybridizes to one of said nucleic acid sequences of interest immediately adjacent to a nucleotide of interest and a constant region comprising a nucleic acid sequence complementary to said detection sequence of the detection probe, and
iv) one or more dideoxynucleotides labeled with an acceptor fluorescent molecule, under conditions suitable for template-dependent single base extension of said primers, wherein said dideoxynucleotides are added to said primers by template-directed extension, thereby forming one or more detection complexes;

b) detecting one or more of said detection complexes of a).

* * * * *

UNITED STATES PATENT AND TRADEMARK OFFICE
CERTIFICATE OF CORRECTION

PATENT NO. : 6,642,001 B1
DATED : November 4, 2003
INVENTOR(S) : Stacey Bolk et al.

It is certified that error appears in the above-identified patent and that said Letters Patent is hereby corrected as shown below:

Column 19,
Line 8, please insert -- 60 -- after the word "about"; and
Line 40, please delete the "-" after the word "acid".

Signed and Sealed this

Twenty-fourth Day of February, 2004

JON W. DUDAS
*Acting Director of the United States Patent and Trademark Office*